United States Patent [19]

Crocker

[11] Patent Number: 5,344,402
[45] Date of Patent: Sep. 6, 1994

[54] LOW PROFILE PERFUSION CATHETER

[75] Inventor: Michael Crocker, Mission Viejo, Calif.

[73] Assignee: Cardiovascular Dynamics, Inc., Irvine, Calif.

[21] Appl. No.: 84,820

[22] Filed: Jun. 30, 1993

[51] Int. Cl.$^5$ .............................................. A61M 29/00
[52] U.S. Cl. ........................................................ 604/96
[58] Field of Search ........................ 604/96, 95, 97–103; 606/194

[56] References Cited

U.S. PATENT DOCUMENTS

| | | |
|---|---|---|
| 3,173,418 | 3/1965 | Baran . |
| 3,769,981 | 11/1973 | McWhorter . |
| 3,834,394 | 9/1974 | Hunter et al. . |
| 3,889,686 | 6/1975 | Duturbure . |
| 4,195,637 | 4/1980 | Gruntzig et al. . |
| 4,417,576 | 11/1983 | Baran . |
| 4,423,725 | 1/1984 | Baran et al. . |
| 4,444,188 | 4/1984 | Bazell ................................ 604/97 |
| 4,573,966 | 3/1986 | Weikl et al. . |
| 4,581,017 | 4/1986 | Sahota . |
| 4,585,000 | 4/1986 | Hershenson . |
| 4,610,662 | 9/1986 | Weikl et al. . |
| 4,661,094 | 4/1987 | Simpson . |
| 4,744,366 | 5/1988 | Jang . |
| 4,762,129 | 8/1988 | Bonzel . |
| 4,763,654 | 8/1988 | Jang . |
| 4,771,777 | 9/1988 | Horzewski et al. . |
| 4,790,315 | 12/1988 | Mueller, Jr. et al. ................. 604/96 |
| 4,832,028 | 5/1989 | Patel . |
| 4,877,031 | 10/1989 | Conway et al. ........................ 604/96 |
| 4,892,519 | 1/1990 | Songer ................................ 604/96 |
| 4,909,252 | 3/1990 | Goldberger ......................... 604/194 |
| 4,944,745 | 7/1990 | Sogard et al. ........................ 604/194 |
| 4,983,167 | 1/1991 | Sahota . |
| 4,995,865 | 2/1991 | Gahara et al. ........................ 604/43 |
| 5,000,734 | 3/1991 | Boussignac et al. . |
| 5,000,743 | 3/1991 | Patel . |
| 5,002,531 | 3/1991 | Bonzel . |
| 5,078,685 | 1/1992 | Colliver . |
| 5,087,247 | 2/1992 | Horn et al. . |
| 5,090,958 | 2/1992 | Sahota ................................ 604/98 |
| 5,090,960 | 2/1992 | Michael . |
| 5,108,370 | 4/1992 | Walinsky . |
| 5,135,474 | 8/1992 | Swan et al. . |
| 5,137,513 | 8/1992 | McInnes et al. . |
| 5,149,330 | 9/1992 | Brightbill . |
| 5,158,540 | 10/1992 | Wijay et al. . |
| 5,160,321 | 11/1992 | Sahota . |
| 5,163,910 | 11/1992 | Schwartz et al. . |
| 5,176,638 | 1/1993 | Michael . |
| 5,195,962 | 3/1993 | Martin et al. . |
| 5,195,971 | 3/1993 | Sirhan ................................ 604/96 |
| 5,201,756 | 4/1993 | Horzewski et al. ................. 604/198 |
| 5,207,650 | 5/1993 | Martin . |
| 5,213,576 | 5/1993 | Abiuso et al. . |
| 5,226,888 | 7/1993 | Arney . |
| 5,232,444 | 8/1993 | Just et al. . |
| 5,254,089 | 10/1993 | Wang . |
| 5,257,974 | 11/1993 | Cox . |
| 5,261,879 | 11/1993 | Brill . |
| 5,279,562 | 1/1994 | Sirhan et al. . |

FOREIGN PATENT DOCUMENTS 0567788 10/1993 European Pat. Off. .
9325265 12/1993 PCT Int'l Appl. .

*Primary Examiner*—J. L. Kruter
*Attorney, Agent, or Firm*—Knobbe, Martens, Olson & Bear

[57] ABSTRACT

Disclosed is a Low Profile Perfusion Catheter, for use in coronary angioplasty applications. Preferably, the catheter is provided with an inflatable dilatation balloon, and a perfusion lumen extending therethrough. The diameter of the perfusion lumen is enlargable from a first, reduced diameter to a second, enlarged diameter. In one embodiment, an axially movable tubular support is movable within the lumen from a proximal, insertion position to a distal perfusion position. In another embodiment, the support is radially expandable. In a further embodiment, a porus drug delivery balloon is provided.

7 Claims, 6 Drawing Sheets

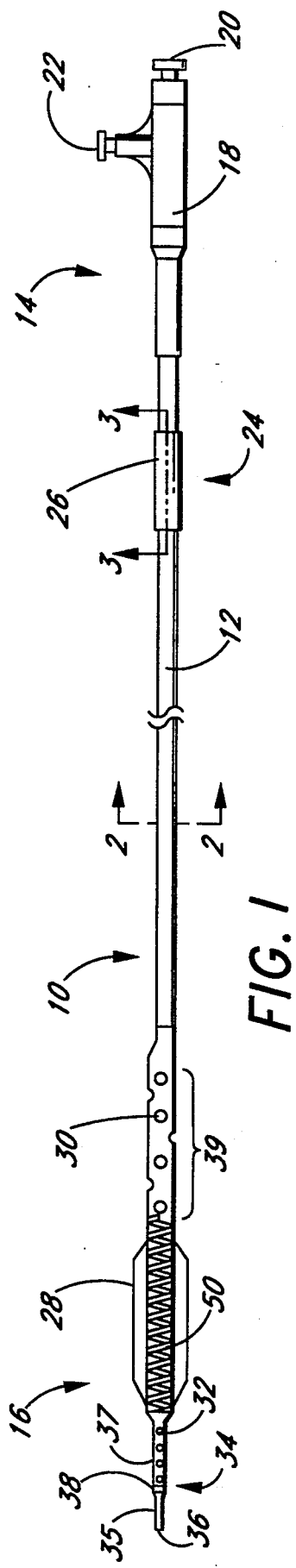
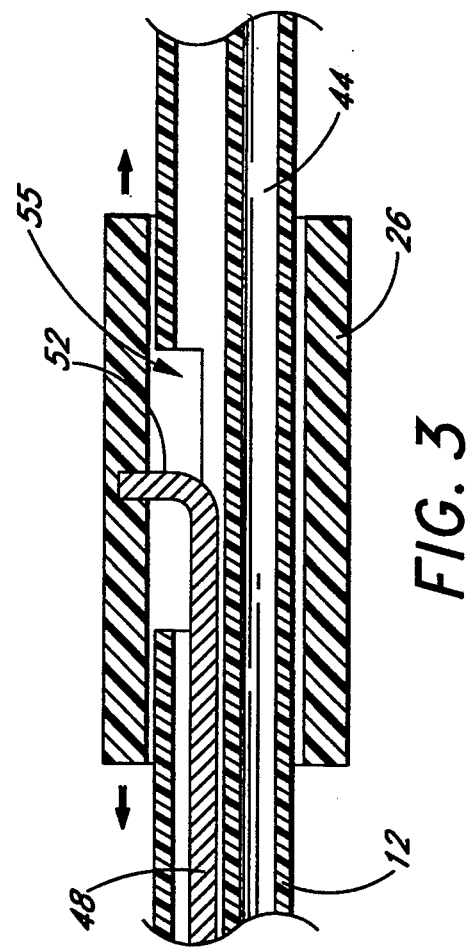
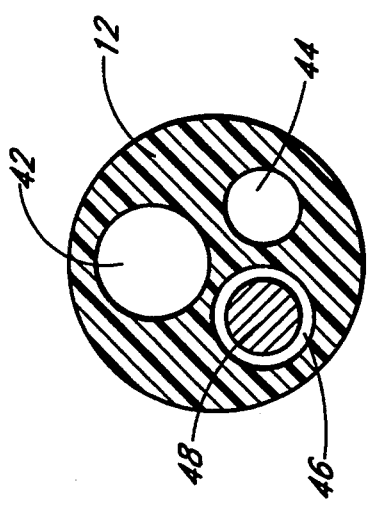

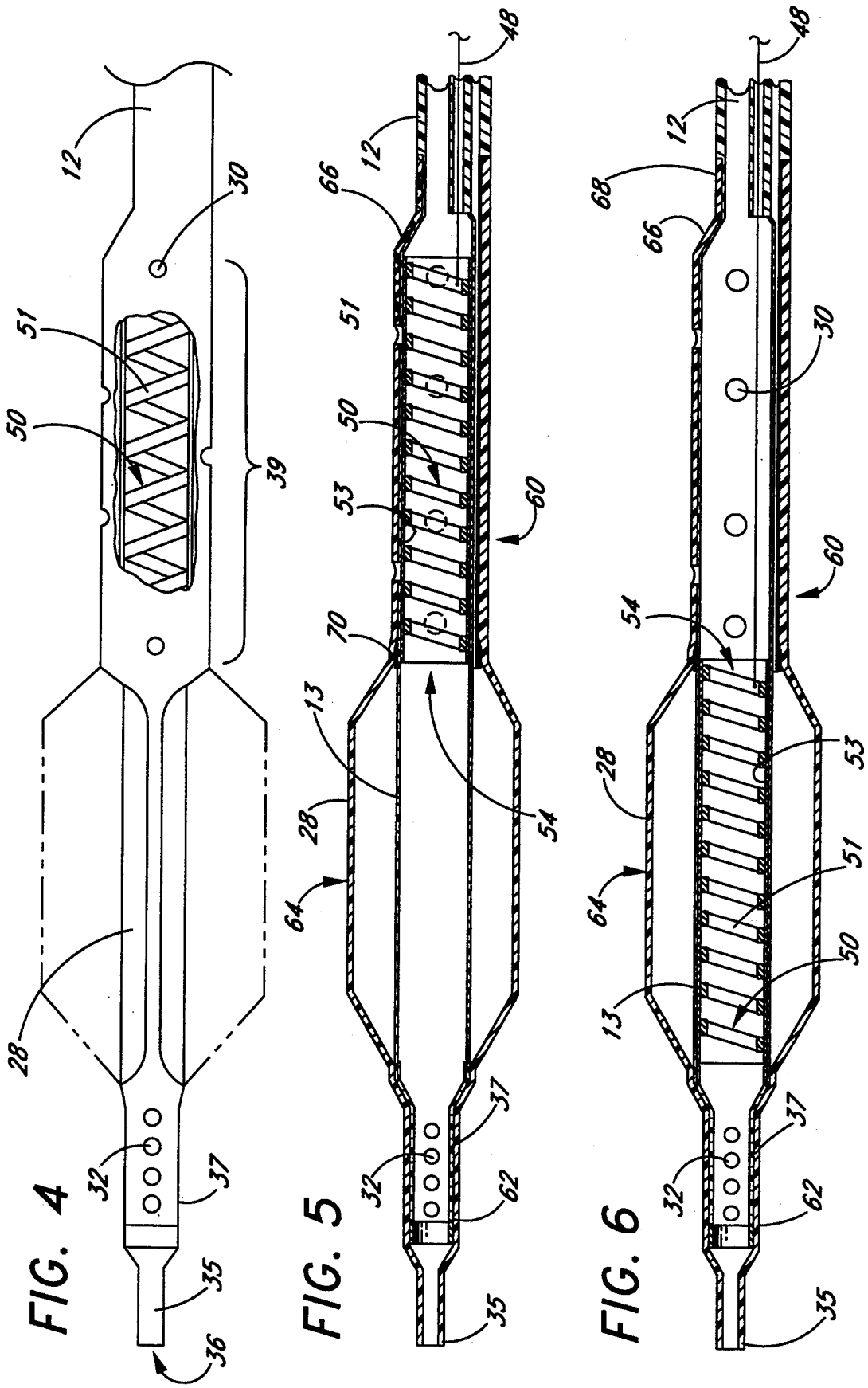

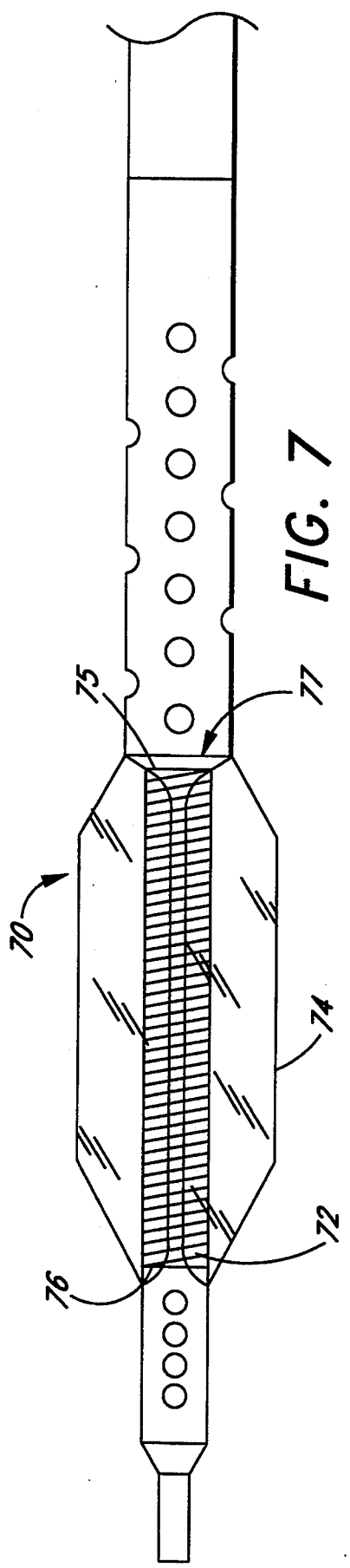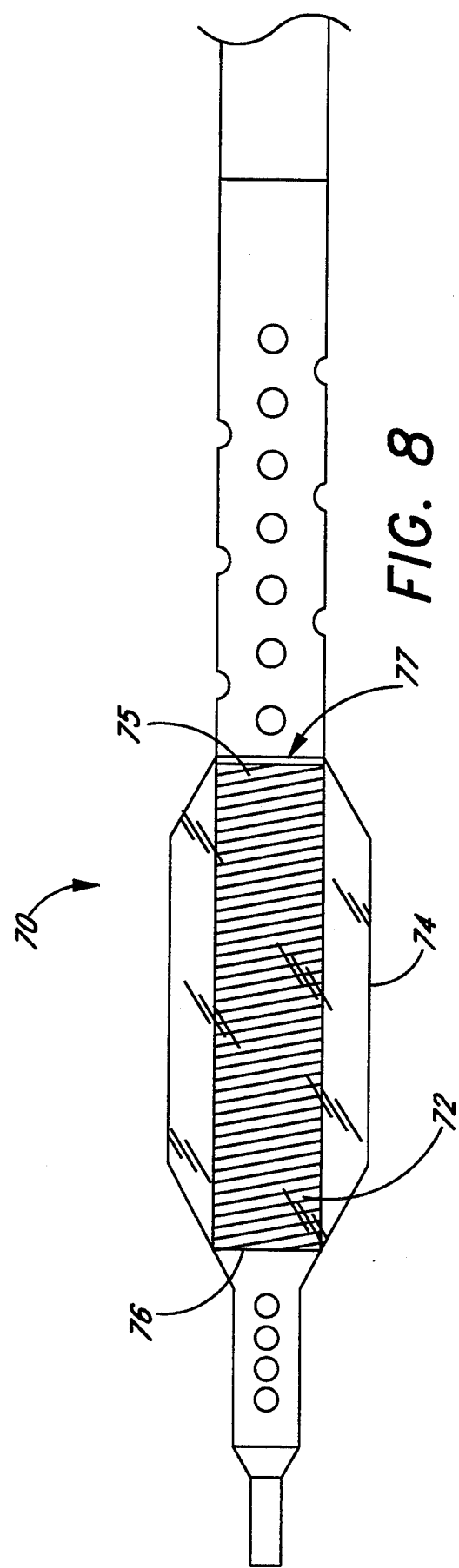

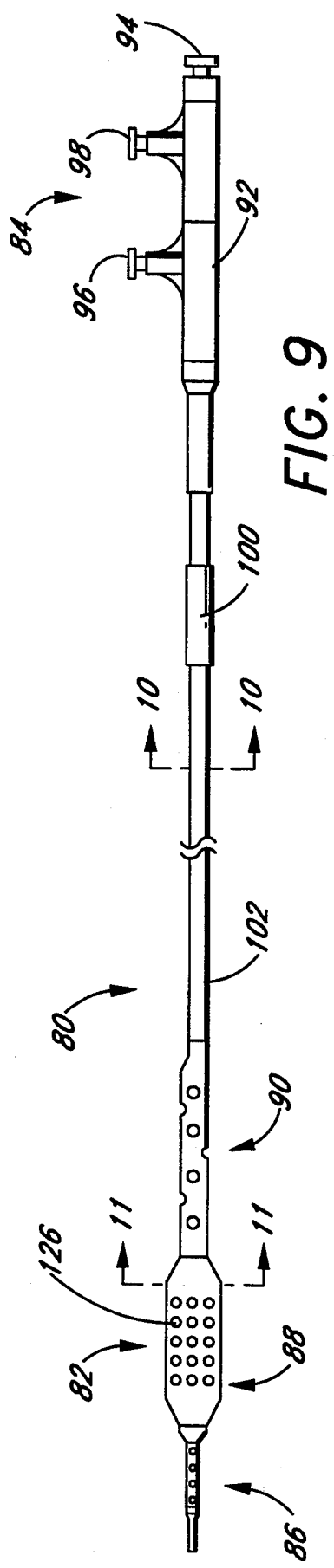
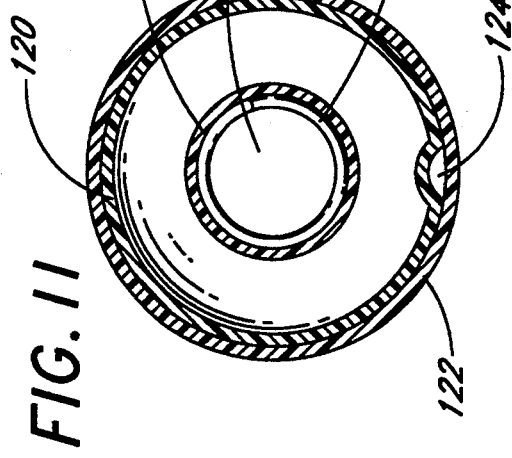
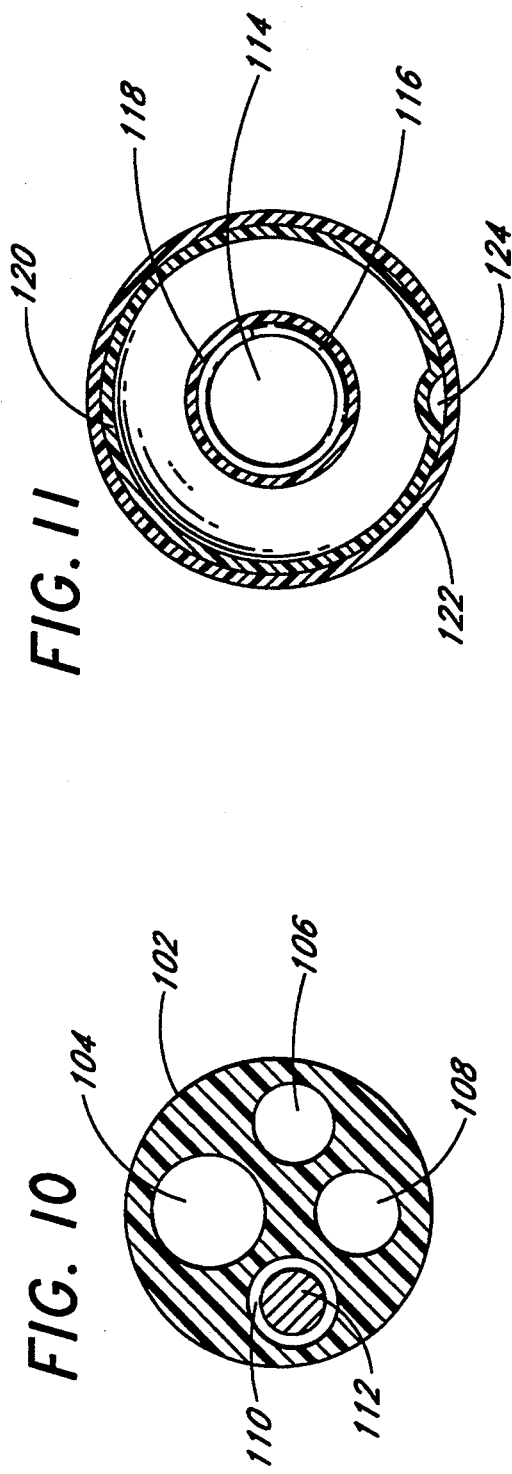

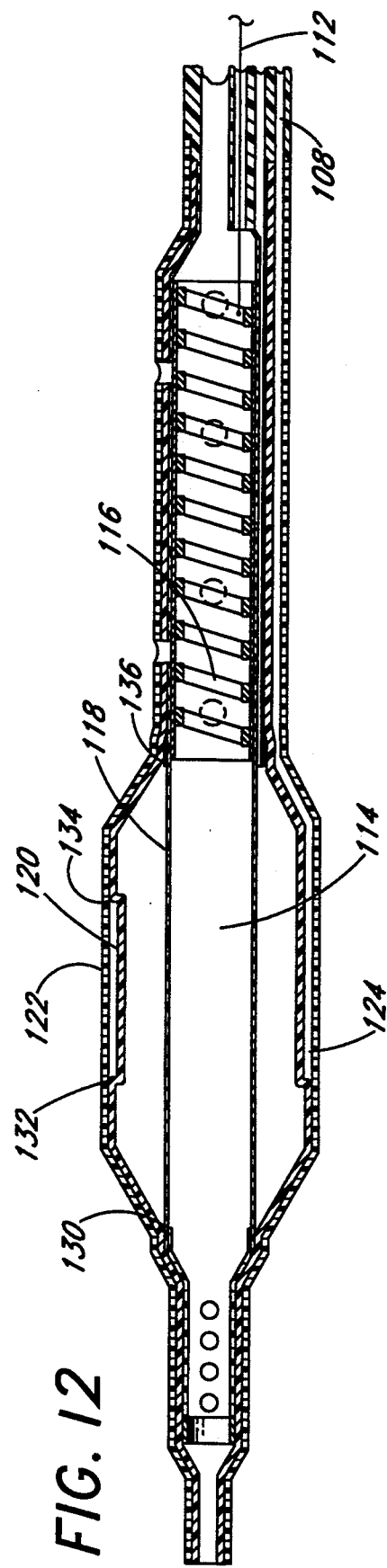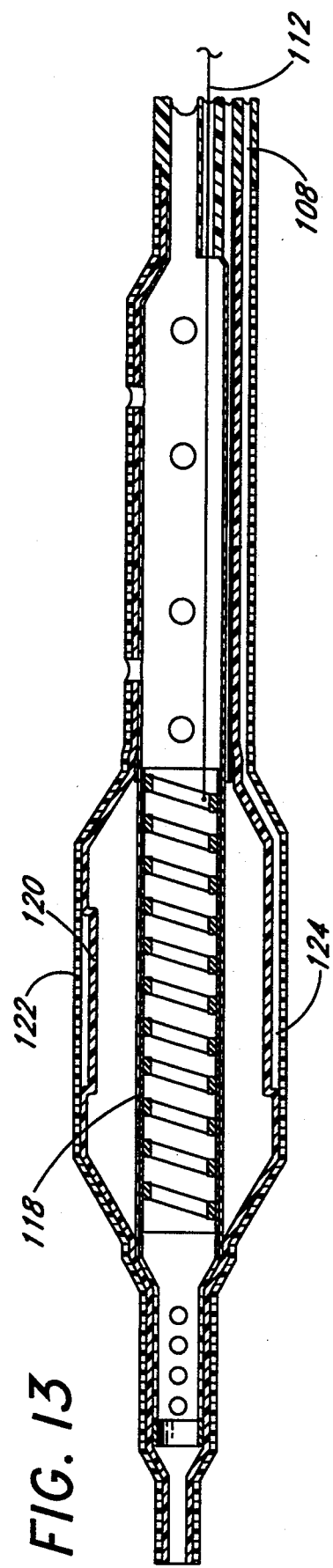

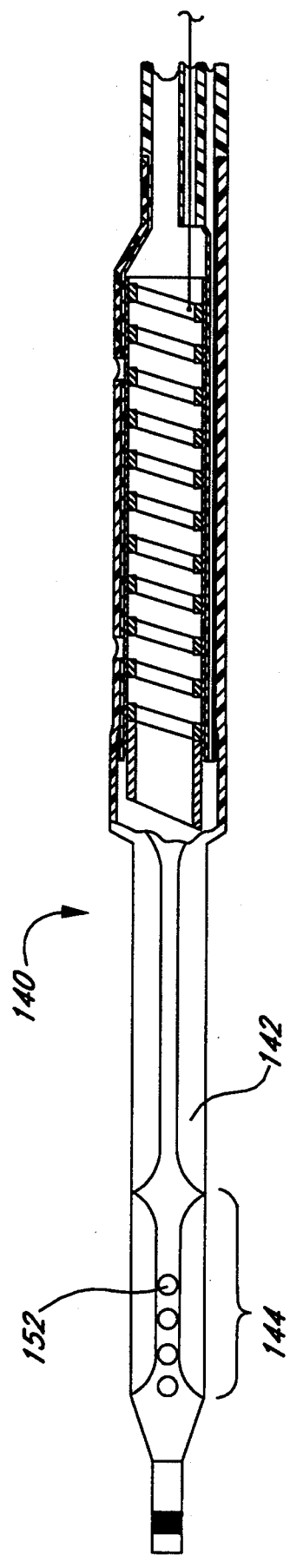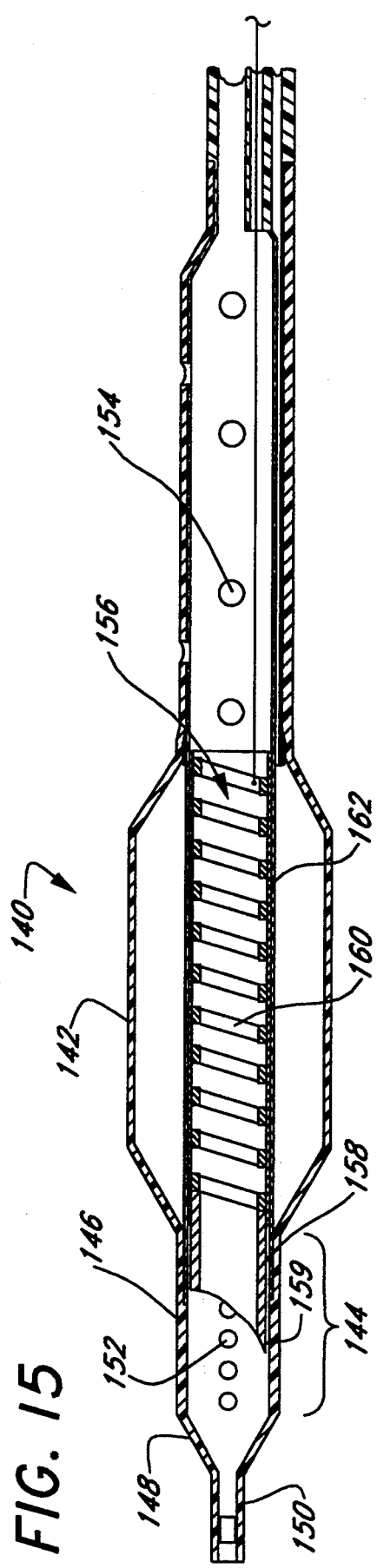
FIG. 14
FIG. 15

LOW PROFILE PERFUSION CATHETER

BACKGROUND OF THE INVENTION

The present invention relates to catheters for insertion into a body lumen. More particularly, the present invention relates to a low profile balloon dilatation and/or drug delivery catheter, having a temporary stent for permitting perfusion while positioned within the vascular system.

A wide variety of catheters have been developed in the prior art for percutaneous transluminal coronary or peripheral vascular applications. For example, balloon dilatation catheters for performing percutaneous transluminal coronary angioplasty ("PTCA") are well known in the art.

In general, PTCA is one procedure for treating a narrowed region in an artery, which, in one form, uses a catheter having an expandable balloon thereon. The catheter is percutaneously inserted such as into the femoral artery, and advanced transluminally until the dilatation balloon is positioned within the restricted portion of the lumen. The balloon is thereafter inflated to radially outwardly displace the obstruction to restore some or all of the original interior diameter of the lumen.

Since this treatment modality requires placement of the deflated balloon across the lesion to be treated, the diameter of the insertion tip of the catheter and deflated profile of the balloon can be limiting factors. This is true either for lesions located in particularly small diameter arteries, or larger diameter arteries having a lesion which occludes a relatively high percentage of the native diameter. Thus, efforts have been in the prior art to produce balloon dilatation catheters having as small a deflated profile as possible.

Other developments in the art include modifying the methodology so that the dilatation balloon remains in an expanded state for a period of time longer than the initial dilatation. Depending upon the medical condition of the patient and clinical judgment, the inflatable balloon may remain in an expanded state for anywhere from several minutes to several hours or longer. Unfortunately, the dilatation balloon necessarily occludes the artery in which it has been expanded, giving rise to a risk of ischemic episodes to the downstream tissue even for relatively short dilatations.

Thus, various efforts have been made in the prior art to produce a balloon dilatation catheter which has some provision for allowing blood flow through or around the balloon during the period of time that the balloon is in the inflated state. Typically, these efforts include the provision of a central through lumen within the balloon, having blood influent ports on one side of the balloon and blood effluent ports on the other side of the balloon. Unfortunately, while these developments may improve the ability to leave the balloon in the dilated state for extended periods, they necessarily enlarge the deflated profile of the balloon catheter. As a result, access to either remote or highly occlusive lesions is limited.

Thus, there remains a need for a catheter which has a minimal deflated or insertion profile for permitting access to remote or highly occlusive lesions, and which at the same time permits sufficient perfusion to minimize the occurrence of ischemic episodes while the balloon is inflated.

SUMMARY OF THE INVENTION

There is provided in accordance with one aspect of the present invention a balloon catheter, such as for performing balloon dilatation procedures in a body lumen. The catheter comprises an elongate flexible tubular body, having an inflatable balloon thereon. At least one influent port is provided on the body on a first side of the balloon, and at least one effluent port is provided on the body on a second side of the balloon. The influent and effluent ports are in fluid communication with each other by way of a central lumen extending through the balloon. An axially movable support is positioned within the central lumen, such that the support is movable from a first, proximal position for installation of the catheter, to a second, distal position for maintaining patency of the central lumen and permitting perfusion while the balloon is inflated.

The central lumen has a first inside diameter when the support is in the proximal position, and a second, larger inside diameter when the support is in the distal position. Preferably, the support comprises a spring coil.

In an over the wire embodiment of the invention, the tubular body is provided with a guidewire lumen extending from a proximal guidewire access port to a distal guidewire opening an the tip of the catheter. In another embodiment of the invention, an access port is provided on the side of the tubular body for providing access to the guidewire lumen at a point in between the inflation balloon and the proximal end of the tubular body, to produce a monorail catheter.

In accordance with another aspect of the present invention, there is provided a balloon catheter comprising an elongate flexible tubular body having an inflatable balloon thereon. The balloon is expandable from a first, reduced diameter to a second, enlarged diameter.

A perfusion conduit extends through the inflatable balloon, and at least a portion of the perfusion conduit is expandable from a first reduced diameter to a second enlarged diameter. Preferably, the second, enlarged diameter of the perfusion conduit is larger than the first, reduced diameter of the inflatable balloon.

Preferably, a tubular support is additionally provided for maintaining the perfusion conduit in the second, enlarged diameter. The support is in one embodiment disposed proximally of the balloon when the balloon is in the first, reduced diameter. The support is movable distally to a position within the balloon to maintain the perfusion conduit in the second, enlarged diameter.

In another embodiment, the support is radially outwardly expandable from a first, reduced diameter, to a second, enlarged diameter. In this embodiment, the support is expanded within the perfusion conduit to maintain the perfusion conduit in the second, enlarged diameter to facilitate perfusion such as during a dilatation procedure.

In accordance with a further aspect of the present invention, there is provided a balloon catheter comprising an elongate flexible tubular body having a central lumen extending through at least a portion of the body. At least one influent port extends through the wall of the tubular body and communicates with the central lumen. At least one effluent port extends through the wall of the tubular body and also communicates with the central lumen. The central lumen is expandable from a first, reduced interior diameter to a second, enlarged interior diameter.

Preferably, a support is provided for maintaining the central lumen in the second, enlarged diameter. The support in one embodiment is axially movable from a first, proximal position to a second, distal position, wherein at least the distal position is within the portion of the central lumen that extends through the balloon. Preferably, the support comprises a spring coil.

In another embodiment, the support is radially outwardly expandable from a first, reduced diameter to a second, enlarged diameter. Preferably, the support comprises a spring coil, and radial expansion is accomplished by relative rotation of one end of the spring coil with respect to the other end of the spring coil.

In accordance with a further aspect of the present invention, there is provided a method of providing fluid flow from at least one influent port on a catheter, through a lumen in the catheter and out at least one effluent port on the catheter.

The method comprises the steps of providing a catheter of the type having an elongate flexible tubular body, at least one influent port on the tubular body and at least one effluent port on the tubular body, said influent and effluent port in fluid communication with each other by way of a central lumen extending through the body.

The catheter is positioned within a body lumen having a fluid therein, and the interior diameter of the central lumen is expanded from a first, reduced diameter to a second, enlarged diameter. Fluid is permitted to enter the influent port, travel through the central lumen in its expanded diameter, and exit the effluent port. Preferably, a support is positioned within the central lumen to maintain the central lumen in the second, enlarged diameter. In one embodiment, the support is positioned within the central lumen by axially distally displacing a movable tubular support.

In accordance with a further embodiment of the present invention, a drug delivery balloon is disposed over the inflation balloon. One or more spots or regions on the inflation balloon are secured to the delivery balloon, so that reduction in the profile of the inflation balloon such as by aspiration causes a reduction in profile of the outer delivery balloon.

Further features and advantages of the present invention will become apparent to one of skill in the art in view of the Detailed Description of Preferred Embodiments which follows, when considered together with the attached drawings and claims.

BRIEF DESCRIPTION OF THE DRAWINGS

FIG. 1 is a side elevational view of a dilatation and temporary stent catheter in accordance with the present invention.

FIG. 2 is a cross sectional view of the catheter taken along the lines 2—2 in FIG. 1.

FIG. 3 is an enlarged cross sectional view through the lines 3—3 on FIG. 1.

FIG. 4 is an enlarged side elevational view of the distal end of the catheter shown in FIG. 1, with the balloon illustrated in the deflated position and the movable support in the proximal position.

FIG. 5 is a side elevational cross sectional view of the distal portion of the catheter, showing the movable support in the proximal position.

FIG. 6 is a side elevational cross sectional view of the distal portion of the catheter, with the movable support in the distal position for maintaining patency of the central lumen within the balloon.

FIG. 7 is a side elevational view of the distal end of an alternate embodiment of the present invention, with the central lumen in a collapsed state.

FIG. 8 is a side elevational view of the embodiment of FIG. 7, shown with the central lumen in the open state.

FIG. 9 is a side elevational view of a drug delivery catheter in accordance with the present invention.

FIG. 10 is a cross sectional view along the lines 10—10 in FIG. 9.

FIG. 11 is a cross sectional view along the lines 11—11 in FIG. 9.

FIG. 12 is a cross sectional elevational view of the distal end of the embodiment of FIG. 9, shown with a tubular support in the insertion position.

FIG. 13 is a cross sectional elevation view as in FIG. 12, with the tubular support in the perfusion position.

FIG. 14 is a cross sectional elevational view of an alternate tip embodiment of the invention, shown in the insertion configuration.

FIG. 15 is a cross sectional elevational view of the embodiment of FIG. 14, shown in the perfusion position.

DETAILED DESCRIPTION OF PREFERRED EMBODIMENT

Referring to FIG. 1, there is disclosed a combination dilatation and temporary stent catheter 10 in accordance with one aspect of the present invention. In other aspects of the present invention, described infra, a drug delivery embodiment is additionally disclosed. Catheters embodying any of the temporary stent, drug delivery and dilatation features disclosed herein, or any combination of these features, will be readily apparent to one of skill in the art in view of the disclosure herein.

The catheter 10 generally comprises an elongate tubular body 12 extending between a proximal control end 14 and a distal functional end 16. The length of the tubular body 12 depends upon the desired application. For example, lengths in the area of about 120 cm to about 140 cm are typical for use in percutaneous transluminal angioplasty applications.

The tubular body 12 may be produced in accordance with any of a variety of known techniques for manufacturing balloon-tipped catheter bodies, such as by extrusion of appropriate biocompatible plastic materials. Alternatively, at least a portion or all of the length of tubular body 12 may comprise a spring coil, solid walled hypodermic needle tubing, or braided reinforced wall, as is well understood in the catheter and guide wire arts.

In general, tubular body 12, in accordance with the present invention, is provided with a generally circular cross-sectional configuration having an external diameter within the range of from about 0.03 inches to about 0.065 inches. In accordance with one preferred embodiment of the invention, the tubular body 12 has an external diameter of about 0.042 inches (3.2 f) throughout most of its length. Alternatively, a generally triangular cross-sectional configuration can also be used, as well as other non-circular configurations, depending upon the method of manufacture and the intended use.

In a catheter intended for peripheral vascular applications, the body 12 will typically have an outside diameter within the range of from about 0.039 inches to about 0.065 inches. In coronary vascular applications, the body 12 will typically have an outside diameter within the range of from about 0.030 inches to about 0.045 inches. Diameters outside of the preferred ranges may also be used, provided that the functional consequences of the diameter are acceptable for the intended purpose of the catheter. For example, the lower limit of the diameter for tubular body 12 in a given application will be a function of the number of fluid or other functional lumen contained in the catheter, together with the acceptable maximum flow rate of dilatation fluid or drugs to be delivered through the catheter, and the desired structural integrity.

Tubular body 12 must have sufficient structural integrity (e.g., "pushability") to permit the catheter to be advanced to distal arterial locations without buckling or undesirable bending of the tubular body. The ability of the body 12 to transmit torque may also be desirable, such as in embodiments having a drug delivery capability on less than the entire circumference of the delivery balloon. Larger diameters generally have sufficient internal flow properties and structural integrity, but reduce perfusion in the artery in which the catheter is placed. Increased diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

The proximal end 14 of catheter 10 is provided with a manifold 18 having a plurality of access ports, as is known in the art. Generally, manifold 18 is provided with a guide wire port 20 in an over the wire embodiment and a balloon inflation port 22. Additional access ports are provided as needed, depending upon the functional capabilities of the catheter.

The proximal end 14 of the catheter 10 is additionally provided with a control 24 for manipulating the axial position of the movable support 50, as will be discussed infra. In the illustrated embodiment, control 24 comprises an axially movable tubular sleeve 26, as will be discussed in connection with FIG. 3.

The distal end 16 of catheter 10 is provided with an inflatable balloon 28, illustrated schematically in FIG. 1. One or more influent flow ports 30 are positioned on the proximal side of balloon 28, for communicating with one or more effluent ports 32 positioned on the distal side of the balloon. The fluid flow direction between the influent port 30 and the effluent port 32 can be readily reversed, as will be apparent to one of skill in the art, depending upon the location of the site to be treated and the direction of access to that site relative to the direction of blood flow.

The distal end 16 of the catheter 10 is provided with an atraumatic distal tip 34, usually having a guide wire exit port 36 as is known in the art. Preferably, a radiopaque marker 38 is provided to facilitate positioning of the catheter, as is known in the art. Suitable marker bands can be produced from a variety of materials, including platinum, gold, and tungsten/rhenium alloy.

The distal tip 34 preferably further comprises a distal introduction segment 35 having an outside diameter within the range of from about 0.020 inches to about 0.030 inches, and a length within the range of from about 2 mm to about 5 mm. In one embodiment, the introduction segment 35 of tip 34 has an outside diameter of about 0.026 inches, and a length of about 2.0 mm.

A perfusion segment 37 is positioned proximally of the introduction segment 35, for carrying one or more effluent ports 32. The length and diameter of perfusion segment 37 can be varied depending upon desired flexibility and perfusion characteristics. In general, an outside diameter within the range of from about 0.03 inches to about 0.04 inches and a length of from about 5 mm to about 10 mm will be used. In one embodiment, the diameter is about 0.033 inches and the length is about 6.5 mm.

The number, size and position of effluent ports 32 can be varied widely within the scope of the invention. In general, the present inventor has found from about 2 to about 10 effluent ports 32 to be workable. Preferably, about six ports each having a diameter of from about 0.014 inches to about 0.021 inches, are used.

Effluent flow ports 32 are placed in fluid communication with the one or more influent flow ports 30 by way of a central lumen 54, as will be discussed infra. In general, central lumen 54 extends axially through the interior of the balloon 28, and also through the interior of the movable support 50 when it is in the distal position. See FIG. 6.

To accommodate the axial movement of the movable support 50 from a proximal, introduction position (FIG. 4) to a distal, perfusion position (FIG. 6), the tubular body 12 is enlarged at an influent region 39, as will be detailed infra. The one or more influent ports 30 are positioned about the periphery of the influent region 39 to permit fluid communication between the influent ports 30 and effluent ports 32 through central lumen 54 when the movable support 50 is in the distal position.

The total number, size and distribution of the influent ports 30 can be varied considerably. In general, between about six and sixty influent ports 30 are preferred and, in one embodiment, thirty influent ports 30 are provided, each having a diameter within the range from about 0.014 inches to about 0.021 inches.

The inflation and temporary stent catheter 10 can be constructed as either an over-the-wire catheter or as a monorail catheter. In a monorail embodiment, the proximal guidewire port 20 can be deleted, and a guidewire access port (not illustrated) is provided at a point in between the balloon 28 and the manifold 18. Preferably, the guidewire port is positioned within the range of from about 10 cm to about 40 cm from the distal end of the catheter. More preferably, the guidewire port is positioned about 30 cm from the distal end. In general, the guidewire port can be positioned as proximally as desired, so long as it does not unduly interfere with the catheter exchange advantage of a monorail catheter on the guidewire. The guidewire port can be positioned as far distally as desired, so long as it does not interfere with the balloon and perfusion features of the catheter, and with the pushability of the catheter on the guidewire.

The guidewire port in a monorail embodiment provides direct lateral access to the interior of guidewire lumen 42, so that a guidewire can be introduced through the monorail port, distally through lumen 42 and out distal guidewire exit port 36 as is known in the art. In a monorail embodiment, the elongate tubular body 12 can be formed in a manner similar to an over the wire embodiment, with guidewire lumen 42 extending throughout the entire length of the tubular body. Preferably, a stiffening wire or other stiffening structure is positioned within guidewire lumen 42 between the guidewire port and the manifold 18. Such a stiffening wire improves the pushability of the catheter, as will be understood by one of skill in the art.

Alternatively, that portion of guidewire lumen 42 proximal to guidewire port can be deleted, provided that the polymer or other support structure in the tubular body 12 has sufficient structural integrity to accomplish the desired result. In this embodiment, the catheter body 12 is provided with two lumen (inflation and push wire) proximally of the guidewire port, and three lumen (inflation, push wire and guidewire) distally of the guidewire port. Additional through lumens, such as for drug delivery, can also be provided as needed.

Referring to FIG. 2, the illustrated over the wire embodiment of tubular body 12 comprises a guidewire lumen 42, a balloon inflation lumen 44, and a push wire lumen 46. In an embodiment of the catheter 10 having a 0.042 inch outside diameter tubular body 12, the guidewire lumen 42 preferably has a diameter of about 0.018 inches. The balloon inflation lumen 44 has a diameter of about 0.013 inches, and the push wire lumen 46 has a diameter of about 0.015 inches.

An axially movable push wire 48 extends axially through push wire lumen 46. Push wire 48 is connected at its proximal end to the control 24, and at its distal end to movable support 50. In the illustrated embodiment, push wire 48 comprises a solid core wire such as a stainless steel wire having a diameter of about 0.012 inches at its proximal portion and a reduced diameter of about 0.006 inches for about the distal most 20 centimeters. Preferably, at least the proximal, larger diameter portion of the push wire 48 is provided with a teflon coating or other coating for minimizing friction within the push wire lumen 46.

Push wire 48 is connected to the moveable support 50 by brazing, soldering or other techniques known in the art and appropriate for the materials to be joined.

The proximal end 52 of push wire 48 can be secured to the push wire control 24 in any of a variety of ways. In the embodiment illustrated in FIG. 3, proximal end 52 extends radially outwardly through an opening 55 in tubular body 12, for connection to the push wire control 24. In this embodiment, push wire control 24 comprises an axially movably disposed tubular sleeve 26 of heat shrink material, such as a polyolefin.

Alternatively, the tubular sleeve 26 may be made from any of a variety of polymeric or metal materials, as long as a sufficient bond or interlocking fit can be provided between the proximal end 52 of push wire 48 and the material of the control 24. Slide switches, buttons or levers may also be used. In practice, the connection between the sleeve 26 and the push wire 48 should be sufficient to permit an axial distal motion, as will be discussed infra, but the ability to axially proximally retract the push wire 48 and movable support 50 is not generally required.

Referring to FIGS. 4-6, the axially movable support feature of the present invention is disclosed. In general, the profile of the deflated balloon limits the catheter's ability to treat lesions in small diameter body lumen. For this reason, the outside diameter of the distal tip 34 and deflated balloon 28 are optimally minimized. At the same time, in order to permit extended periods of dilatation, a temporary stent or conduit is preferably provided to permit continued blood flow during the dilatation. This tends to require a central through lumen in the balloon, which increases the profile of the deflated balloon.

In accordance with the present invention, a movable support 50 is provided, for defining a central lumen 54. The movable support 50 is axially movable from a first, proximal position (FIGS. 4 and 5) to a second, distal position (FIG. 6). While the support 50 is in the proximal position, the deflated balloon 28 has a minimal profile to facilitate positioning adjacent an obstruction in a small diameter artery. Preferably, the deflated profile of the balloon is less than about 0.040 inches, and, more preferably, the deflated profile of a 3 mm inflated diameter balloon is less than about 0.034 inches.

Following positioning of the balloon within a restricted portion of the artery, the movable support 50 is advanced distally to the second position within the balloon. In the illustrated embodiment, movable support 50 provides a central lumen 54 through the balloon 28 having an interior diameter of about 0.039 inches, which is generally larger than the exterior deflated profile of the balloon when the support 50 is in the proximal position.

The movable support 50 preferably comprises a support structure for resisting radial compression of central lumen 54 by the inflated balloon 28. Suitable support structures include tubular bodies which may comprise extrusions, braided or woven polymeric or metal reinforcement filaments, or a spring coil 51. Spring coil 51 preferably comprises a material having suitable biocompatibility and physical properties, such as stainless steel or platinum wire. Alternatively, polymeric materials, such as nylon or Kevlar (DuPont) may also be used. Preferably, rectangular ribbon is used, having cross-sectional dimensions on the order of about 0.001 inches by about 0.003 inches for small vessels, and on the order of about 0.005 inches by about 0.010 inches for use in larger vessels.

The wire or ribbon is preferably wound to produce a coil having an interior diameter within the range of from about 0.030 inches (coronary) to about 0.100 inches (peripheral) and an exterior diameter within the range of from about 0.032 inches (coronary) to about 0.110 inches (peripheral).

Spring coil 51 may be either tightly wound (bottomed out) so that adjacent loops of coil are normally in contact with each other, or loosely wound, as illustrated in FIGS. 5 and 6, in which the adjacent loops of coil are normally separated from one another. The selection of a tightly wound or loosely wound coil for use in the present invention will be influenced by such factors as the desired weight of the finished catheter, the relative desired flexibility of the catheter in the region of the movable support 50, and the amount of radially inwardly directed compressive force exerted by the inflation balloon 28. Radiopacity may also be a factor.

Preferably, spring coil 51 is provided with an outer sheath or coating 53. Sheath 53 may be produced by dipping, spraying, heat-shrinking or extrusion techniques, which are understood in the art, and preferably comprises a relatively flexible material having sufficient biocompatibility and relatively low friction at its contact surface with the interior of the catheter 10. Suitable materials for sheath 53 comprise linear low-density polyethylene, such as that produced by Dow, polyethylene teraphthalate, nylons, polyester or other known or later developed medical grade materials. In one embodiment, a polyethylene tube having a wall thickness of about 0.002 inches and native diameter of about 0.050 inches is positioned coaxially about a 0.043 inches O.D. spring coil and reduced in diameter by application of heat to produce a tight fit over the spring coil.

A central cavity for receiving the moveable support 50 can be formed in any of a variety of ways. In accordance with one method of manufacturing the catheter 10, approximately the distal most 5 centimeters of the guidewire lumen 42 are enlarged to an interior diameter of about 0.050 inches by thermal blow molding the catheter body. The resulting thickness of the wall 13 is about 0.001 inches. In the illustrated embodiment, this enlarged diameter is maintained for approximately 4 centimeters, at which point the distal tip assembly 34 is provided.

The flexibility of the tubular wall 13 extending through the interior of balloon 28 permits the central lumen 54 to be collapsed to provide a minimal profile for insertion and positioning of the catheter. Following insertion of the catheter, tubular wall 13 can be reexpanded to its original interior diameter such as by fluid flow, or by positioning of the support 50 as described elsewhere herein. Patency of the central lumen 54 through tubular wall 13 is thus restored by and/or maintained by support 50.

Although the present description will periodically refer to a first reduced diameter of the central lumen 54 and a second expanded diameter of the central lumen 54, that is intended to include also a first collapsed state and second open state. In general, the wall 13 comprises a substantially inelastic material so that actual expansion of the wall is not ordinarily accomplished. The feature sought to be accomplished by the collapsible wall 13 is a reduced exterior profile for insertion of the catheter, and a later increased fluid flow capacity through the central lumen 54 as will be apparent in view of the disclosure herein.

In general, it is desired that the ratio of the interior cross-sectional area of lumen 54 to the maximum exterior cross-sectional area of the deflated balloon be maximized, in order to optimize perfusion through the balloon 28 while inflated. Catheters embodying the present invention, and having a cross-sectional profile through the stent 50 of about 0.055 inches (4.2 f) can be produced having a central lumen 54 with an interior diameter of at least about 0.030 inches, and preferably about 0.039 inches or greater. This still fits readily within the lumen of a typical guide catheter, which may have an internal diameter of about 0.072 inches.

In one embodiment of the present invention, the interior diameter of lumen 54 is about 0.039 inches. This lumen will typically provide a flow at 80 millimeters Hg of approximately 50 milliliters per minute. Alternatively, the inside diameter of lumen 54 can be reduced to as low as about 0.012 inches and still function as a guidewire conduit.

Dilatation balloon 28 generally comprises a proximal neck portion 60, a distal neck portion 62, and an intermediate dilatation portion 64. The proximal neck portion 60 is conveniently extended for at least about 2 to 3 centimeters in the proximal direction. In the illustrated embodiment, proximal neck 60 extends proximally for at least about the 2.0 centimeter length of the support 50. Preferably, neck portion 60 extends an additional 2 centimeters overlapping the tapered section 66, and as much as an additional 5 centimeters or more at 68 along the length of tubular body 12. The proximal neck portion 60 is conveniently secured such as by heat shrinking, as will be understood in the art.

In one embodiment of the invention, both the tubular body 12 and the balloon 28 comprise crosslinked medium density polyethylene. As a consequence, the heat shrunk proximal neck 60 does not form a strong bond with the wall adjacent thereto. In order to prevent the pressure of the inflated balloon 28 from peeling the proximal sleeve 60 apart from the adjacent wall 13, an annular band 70 of non-crosslinked medium density polyethylene is provided, to permit bonding of the proximal sleeve 60 to the tubular wall 13. Band 70 in one embodiment is in the form of a 0.050 inch inside diameter by 0.054 inch length annular ring. The same construction preferably is used at the distal end of the balloon as well.

In a preferred embodiment of the illustrated design, the dilatation balloon comprises a relative non-elastic material, such as medium density polyethylene, linear low density polyethylene, polyethylene teraphthalate, nylon, polyester, or any of a variety of other medical grade polymers known for this use in the art. Preferably, the geometry, materials and seals of the balloon 28 will withstand an internal pressure of at least about 10 atmospheres without any leakage or rupture.

Balloon 28 is preferably pre-molded to have an inflated diameter in a catheter intended for peripheral vascular applications within the range of from about 1.5 millimeters to about 8 millimeters. The balloon 28 in a catheter intended for coronary vascular applications preferably has an inflated diameter within the range of from about 1.5 millimeters to about 4 millimeters.

The distal sleeve 62 of balloon 28 is heat shrunk over the distal tip of the catheter, and may take any of a variety of forms, depending upon the distal tip construction.

The basic method of the present invention can be accomplished by any of a variety of structures which permit a perfusion conduit within a catheter to be enlarged from a first, reduced cross sectional area to a second, enlarged cross sectional area. Preferably, as has been described, a support structure is provided for maintaining the perfusion lumen in the second configuration.

Referring to FIGS. 7 and 8, there is disclosed an alternative support structure for maintaining patency of the perfusion conduit. FIG. 7 illustrates a representational view of a radially enlargable tubular support 72 disposed within the balloon region 74 of a dilatation and/or drug delivery catheter 70. The radially enlargable support 72 preferably comprises a coil having a proximal end 75, a distal end 76 and a central flow passageway 77 extending axially therethrough. The support member 72 may therefore be radially reduced or enlarged by rotating one end of the coil relative to the other, as will be understood by one of skill in the art.

The construction and design details of the catheter illustrated schematically in FIGS. 7 and 8 is in many ways similar to the embodiment illustrated in FIG. 6. However, rather than axial movability of the support structure 50 illustrated in FIG. 6, the support structure 72 of FIGS. 7 and 8 is preferably permanently positioned within the inflation balloon 74. In one embodiment, the proximal end of the support structure 72 is secured against rotation with respect to the catheter body. The distal end of the support structure 72 is secured to a rotatable wire which extends axially throughout the length of the catheter to a proximal source of rotational energy. Rotation of the wire causes a radial enlargement or reduction of the profile of the catheter beneath the balloon 74.

The source of rotational energy can either be a finger manipulable wheel, or other structure for permitting rotation of the wire, either directly, or through a gear train to provide a rotational advantage at the distal end.

Prior to installation of the support member 72, an outer tubular sleeve is preferably heat shrunk over the loops of the coil, while the coil in its radially enlarged configuration. The coil is thereafter converted to its reduced profile, for installation and positioning of the catheter. In one embodiment, the native diameter of the coil is the reduced diameter as illustrated in FIG. 7. In this embodiment, a rotational force is required to wind the spring up to its enlarged diameter configuration. Alternatively, the native diameter of the coil is the enlarged flow capacity configuration, so that the coil may be wound down to its reduced profile for insertion, and then released so that it returns to its enlarged cross sectional area configuration under its own force.

Referring to FIG. 9, there is disclosed an elongate tubular drug delivery and balloon dilatation catheter 80 in accordance with a further aspect of the present invention. The catheter 80 generally comprises a tubular body 102 having a distal functional end 82, and a proximal control end 84.

Distal end 82 generally comprises a distal tip assembly 86, disposed distally of a combination inflation and drug delivery balloon assembly 88. Distal tip assembly 86 is provided with a tip as previously discussed, and a plurality of perfusion ports 126. Proximal to the balloon assembly 88 is an influent region 90, which is preferably also adapted to receive a movable support when the catheter is in an insertion mode, as has been previously discussed.

Proximal end 84 generally comprises a manifold 92, having a guidewire lumen access port 94 thereon. In addition, an inflation port 96 is provided for allowing fluid communication with the inflation balloon 120. An infusion port 98 is also provided, for permitting infusion of a gas or fluid such as a medication to be delivered through the distal end 82 of the catheter.

A control 100 is mounted on the catheter body 102, for controlling the axial position of the movable support as has been discussed in connection with previous embodiments.

As illustrated in FIG. 10, the tubular body 102 is provided with an axially extending guidewire lumen 104, for conducting a guidewire through the catheter body and out the distal end as has been discussed. Although the drug delivery catheter 80 illustrated in FIG. 9 is an over the wire embodiment, the catheter can be readily converted to a monorail embodiment by one of skill in the art.

In a monorail type exchangeable catheter embodiment, an access port (not illustrated) is provided along the tubular body 102 in between the influent region 90 and the manifold 92. That access port provides access through the wall of the tubular body 102 and into guidewire lumen 104 as is known in the art. Preferably, the access port is positioned within the range of from about 10 cm to about 40 cm from the distal tip of the catheter.

In a monorail embodiment, the portion of the guidewire lumen 104 disposed proximally of the access port is preferably filled with a stiffening rod, or polymer, as has been discussed, to improve the pushability and other physical properties of the catheter body. Alternatively, the tubular body 102 can be extruded in a manner that eliminates the portion of the guidewire lumen 104 disposed proximally of the monorail guidewire access port.

A balloon inflation lumen 106 extends axially through the tubular body for providing fluid communication between the balloon inflation port 96 and the inflation balloon 120 as will be discussed. In addition, an infusion lumen 108 extends axially through the tubular body 102, for providing fluid communication between the infusion port 98 and one or more drug delivery ports 126 disposed on the distal portion 82 of the catheter 80.

An axially extending push wire lumen 110 is provided for axially movably receiving the push wire 112. Push wire 112 mechanically links the control 100 with the movable support, as has been discussed in previous embodiments.

Referring to FIG. 11, a central perfusion lumen 114 is defined within collapsible tubular wall 118, surrounding the support 116. Although illustrated in FIG. 12 in an enlarged configuration, the tubular wall 118 will normally be partially or completely collapsed when the support 116 is in the proximal insertion position. In the illustrated embodiment, patency of the perfusion lumen 114 is restored and/or maintained by advancing the support 116 distally into the perfusion position. Patency of the perfusion lumen can also be optimized using alternate support structures such as a radially expandable structure of the type illustrated in FIG. 7 and 8.

An inflatable balloon 120, illustrated in the inflated position, is disposed within an outer delivery balloon 122. Inflatable balloon 120 and delivery balloon 122 will be described in detail infra. The delivery balloon 122 is supplied with a media to be delivered such as a fluid medication by way of infusion lumen 108 and a delivery lumen 124 extending between the inflation balloon 120 and delivery 122. See FIGS. 11 through 13.

In a preferred embodiment of the illustrated design, the inflation balloon comprises a relatively nonelastic material such as linear low density polyethylene, polyethyleneteraphthalate, nylon, polyester, or any of a variety of other medical grade polymers known for this use in the art. Preferably, the geometry, material and seals of balloon 30 will withstand an internal pressure of at least about 5 atmospheres for drug delivery applications, and, preferably at least about 10 atmospheres for dilation and drug delivery applications, without any leakage or rupture.

Balloon 120 is preferably premolded to have the same inflated diameters as discussed in connection with previous embodiments. Construction materials and other design parameters can be readily modified by one of ordinary skill in the art, depending upon the intended use of the catheter. In particular, balloon 120 can be constructed in a manner that is suitable for use in dilatation procedures, such as is well known in the art of percutaneous transluminal coronary angioplasty and other applications in which dilatation of stenotic region in a body lumen is desired. Alternatively, the balloon 120 may merely be desired to provide sufficient radially expansive force to compress the drug delivery balloon 122 against the wall of the vessel. In this intended use embodiment, considerations appropriate for a lower pressure system may be utilized.

The drug delivery balloon 122 is most conveniently disposed radially outwardly from the inflation balloon 120. Drug delivery balloon 122 may comprise a generally nonelastic material such as is conventional for angioplasty dilatation balloons, or may alternatively comprise an elastic material such as latex or urethane, or any of a variety of other suitably biocompatible elastomers. Use of an elastic material for drug delivery balloon 122 can assist in reducing the relatively rough edges of the collapsed inflation balloon 120, and thereby reduce trauma to the vascular intima during insertion and withdrawal of the catheter.

Drug delivery balloon 122 is provided with a plurality of delivery ports 126. Delivery ports 126 may be disposed radially symmetrically about the outer periphery of the delivery balloon 122, or may be limited to only portions of the exterior surface of the delivery balloon 122 depending upon the desired drug delivery pattern. For example, delivery ports 126 can be positioned along a single line extending axially along the balloon, or on one hemisphere of balloon 122. Alternatively, delivery ports 126 can extend for less than the entire length of the balloon.

Delivery balloon 122 alternatively comprises a material which is inherently permeable, without the provision of discrete delivery ports 126. For example, woven or braided filaments or fabrics can be used. For relatively low delivery rate applications, fluid permeable membranes can also be used.

As can be seen with reference to FIGS. 9 through 12, drug or other fluid introduced through infusion port 98 is conducted by way of infusion lumen 108 and 124 into the interior of drug delivery balloon 122. The inflated volume of inflation balloon 120 causes the drug to be expelled by way of ports 126 outside of the drug delivery system.

Preferably, the relative inflated dimensions of the delivery balloon 122 and the inflation balloon 120 are such that a minimum amount of drug is retained between the two balloons. Thus, preferably, the inflated inflation balloon 120 substantially completely fills the interior chamber of the drug delivery balloon 122 to efficiently expel essentially all of the fluid introduced into balloon 122 by way of drug delivery lumen 108. Residual volume of drugs contained in lumens 108 and 124 can be expelled outside of the balloon 122 such as by following the drug with a small volume of normal saline or other "rinse" solution, as will be understood by one of skill in the art.

In a further alternative, the inflation and drug delivery are accomplished by the same balloon. In this embodiment, the permeability rate of the balloon material, or the diameter and number of delivery ports 126 are sufficiently small that the balloon 122 is sufficiently firmly inflated without delivery at an excessive rate. Appropriate permeability rates for the balloon material can be determined through routine experimentation, in view of such factors as the viscosity of the drug, desired delivery rate, and the desired radially expansive force to be exerted by the balloon.

The catheter 80 can be manufactured in accordance with the techniques described in connection with previous embodiments, with the outer delivery balloon heat shrunk or otherwise positioned over the inflation balloon. The inflation balloon can be manufactured in any of a variety of manners which are now conventional in the art, such as free-blowing polyethylene, polyethyleneteraphthalate, nylon, polyester, or any of a variety of medical grade polymers known for this use.

Generally, the delivery balloon is produced by blowing sections of cross-linked polyethylene within a tubular mold to control the outside diameter. The outside diameter of the section is generally within the range of from about 1.5 mm to about 5.0 mm for use on a 0.042 inch diameter catheter body.

The section of delivery balloon material is thereafter heat stretched at the proximal and distal necks down to a thickness of about 0.001 inches and a diameter which relatively closely fits the portion of the catheter body to which it is to be sealed. The appropriate length is cut, depending upon the desired length of the balloon and balloon delivery region, and the desired balloon neck length in the finished product.

The proximal neck is heat sealed around the catheter body 102 and inflation balloon 120. In general, the length of the proximal neck of the delivery balloon is within the range of from about 1 cm to about 5 cm inches, or longer, depending upon desired flexibility and other characteristics. The delivery lumen 124 is formed by placing a mandrel in between the two balloons prior to the final heat shrinking step of the proximal neck portion, and thereafter removing the mandrel following the heat shrinking step. The distal neck is thereafter heat shrank to the desired configuration.

In an embodiment utilizing cross-linked polyethylene for both the inner inflation balloon and outer delivery balloon, the delivery balloon may be secured to the axial ends of the inflation balloon through the use of a UV curable adhesive, due to the difficulty in thermally bonding cross-linked polyethylene to cross-lengthened polyethylene.

However, it is to be understood that the material utilized for the outer delivery balloon may be varied considerably, and the term balloon as used in the context of the delivery "balloon" 122 is intended to be only generally descriptive of this structure as has been discussed.

Referring to FIG. 12, the inflation balloon 120 and delivery balloon 122 are secured together in at least a sufficient manner to permit the deflation of inflation balloon 120 such as by aspiration to pull the delivery balloon 122 into a retracted profile. This is accomplished in the illustrated embodiment by securing portions of the inflation balloon 120 to the delivery balloon 122 such as in the region between a distal point of attachment 130 and an intermediate point of attachment 132.

In addition, a proximal zone of the delivery balloon is also preferably secured to the inflation balloon such as between an intermediate point 134 and proximal point of attachment to the catheter body 136. This construction leaves a delivery zone of at least that region on the delivery balloon between points 132 and 134. The width of this delivery zone can be increased or decreased as desired, depending upon the desired delivery profile.

In an embodiment having a balloon length of about 2.6 cm from point 130 to point 136, the delivery zone (132 to 134) will normally be about 1 cm in length. In addition, alternate structures such as adhesive bands, spot seals, welds, or other manners known to those of skill in the art can be utilized to cause the outer delivery balloon 122 to reduce in profile in response to the aspiration of inflation balloon 120.

Referring to FIGS. 14 and 15, there is shown an embodiment of a dilatation and perfusion catheter design having an alternate tip design. The embodiment of FIGS. 14 and 15 can be readily modified to additionally include a drug delivery capability in accordance with the disclosure herein by one of skill in the art.

Referring to FIG. 14, there is disclosed an inflation and perfusion catheter 140, having an inflatable balloon 142 shown in the deflated, low profile configuration. The principal difference between this embodiment and that disclosed in FIGS. 4 through 6 occurs in the perfusion segment 144.

The perfusion segment 37 in FIGS. 4 through 6 is illustrated as having a diameter which is unchanged between the insertion configuration of the catheter and the perfusion configuration of the catheter. However, the perfusion segment 37 in this design can become the perfusion flow rate limiting structure when the catheter is in the perfusion position. The alternate tip design of FIGS. 14 and 15 permit a perfusion segment 144 to change between a low profile, insertion configuration shown in FIG. 14, and an enlarged, increased fluid flow capacity configuration as shown in FIG. 15 for maximum perfusion.

The collapsible perfusion segment 144 can be constructed in any of a variety of ways and accomplish the optimized perfusion advantage of the present invention. In the embodiment illustrated in FIG. 15, the material of balloon 142 extends in the form of an elongated distal neck 146 which is preferably reduced by taper 148 to form an introduction segment 150 as has been described. The wall 146 of perfusion segment 144 exhibits a similar flexibility to the wall of balloon 142. Perfusion segment 144 is additionally provided with a plurality of perfusion openings 152 for communicating with a plurality of perfusion openings 154 by way of a central lumen 156 as has been described in connection with previous embodiments.

The illustrated embodiment is provided with an axially movable support 160, illustrated in the form of a spring coil. The support 160 is preferably capable of extending a sufficient distance into the perfusion segment 144 to open the interior lumen of the perfusion segment 144 when the support 160 is advanced into the distal position. The distal extension of the support 160 may take a variety of forms, such as an extension of the spring coil beyond the distal end of the balloon 142.

Alternatively, as illustrated in FIGS. 14 and 15, a distal leader segment 158 is provided. Leader segment 158 preferably comprises a solid wall tubular member, such as a section of polymeric extrusion or shrink wrap tubing, which is secured to the distal end of the spring coil by an outer shrink wrap tubing layer 162. Preferably, the leader segment 158 is provided with a wedge shaped distal tip 159, to facilitate opening the central lumen within the perfusion segment 144 upon distal repositioning of the support member 160. A variety of other leader segments for maintaining patency of the perfusion segment 144 can be constructed which will accomplish the function achieved by the present invention. Thus, for example, two-piece or one-piece integral support structure 160 and leader segment 158 can be readily constructed in a variety of configurations. Advantageously, this embodiment permits a minimal profile for both the balloon segment and the distal perfusion segment 144 for insertion of the catheter into a small opening, yet permits maximum perfusion therethrough when the catheter is moved to the perfusion configuration.

In accordance with a method of the present invention, a site is identified in a body lumen where it is desired to deliver an amount of a medication or other fluid. For example, thrombolytic or restenosis inhibiting drugs may be desirably introduced directly to the affected wall following dilatation. Alternatively, anticoagulants, plaque softening agents or other drugs may be desirably delivered directly to the site of a thrombosis or other vascular anomaly.

A conventional angioplasty guidewire is percutaneously transluminally inserted and advanced to the desired treatment site. Guidewires suitable for this purpose are commercially available, having a variety of diameters such as 0.014 inches.

The distal end of any of the catheters disclosed herein is threaded over the proximal end of the guidewire, once the guidewire has been positioned within the desired delivery site. The catheter is thereafter advanced distally along the guidewire in a conventional manner, until the drug delivery balloon 122 is disposed adjacent the desired delivery site. Thereafter, a suitable inflation fluid such as a radiopaque solution is introduced by way of inflation port 96 and into the inflation balloon 120 to press the delivery balloon 122 against the vascular wall. As described previously herein, the catheter of the present invention may additionally be used to perform dilatation, if desired.

Either prior to, during or following dilatation of inflation balloon 120, the tubular support structure 116 is preferably positioned to maintain or restore patency to central lumen 114. In the illustrated embodiment, for example, this is accomplished by moving the tubular support structure 116 distally to a perfusion position within the inflation balloon 120.

Once the drug delivery balloon 122 has been positioned adjacent the vascular wall, and the tubular support structure 116 positioned within the central lumen 114, medication is infused for expulsion by way of drug delivery ports 126 directly against the vascular wall. Medication can be introduced under gravity feed alone, or by way of a pressure pump, as desired by the clinician in view of such factors as drug viscosity, toxicity and desired delivery rate.

In this manner, drugs can be permitted to be absorbed into the affected site, with a minimal amount drug escaping into generalized circulation. At the same time, perfusion beyond the delivery balloon is optimized by way of the central lumen 114.

The rate of drug delivery is somewhat limited by the rate of absorption by the vascular wall, and delivery rates on the order of about 30 ml per hour to about 20 ml per minute are presently contemplated for use in the method of the present invention. Certain medications may be optimally delivered at much lower rates, as well, such 1 ml per day or lower. However, these rates may be modified significantly, depending upon the drug, and the extend to which "overflow" fluid is permitted to escape into the circulatory system.

In either the balloon dilation or the drug delivery applications, the catheter may desirably remain indwelling and inflated for an extended period of time. Perfusion past the inflation balloon by way of a temporary stent of the type disclosed herein minimizes the adverse impact on circulation due to the indwelling catheter. Following infusion of the predetermined volume of drug, or the desirable dilatation period and/or post dilatation period, the balloon may be deflated and the catheter proximally withdrawn from the treatment site in a conventional manner. Generally, there is no need to return the tubular support structure 116 or 50 to the proximal insertion position in order to accomplish removal of the catheter.

The basic methodology for use of the present invention in a balloon dilatation procedure, or a post-dilatation treatment include the steps of positioning the balloon within the treatment site, while the tubular support structure is in the insertion position, thereafter advancing the tubular support structure distally into the perfusion position. Alternatively, the tubular support structure is enlarged radially outwardly or otherwise moved from the insertion position to the perfusion position depending upon the structure of the tubular support structure.

Thereafter, the inflation balloon is inflated or permitted to remain inflated for a sufficient balloon dilatation or post-dilatation period. The inflation balloon is subsequently deflated, and the catheter is removed in accordance with conventionally techniques.

Although this invention has been described in terms of certain preferred embodiments, other embodiments that are apparent to those of ordinary skill of art are also within the scope of the invention. Accordingly, the scope of the invention is intended to be defined only by reference to the appended claims.

What is claimed is:

1. A balloon catheter, comprising:
    an elongate, flexible, tubular body;
    an inflatable balloon on the tubular body, said balloon expandable from a first, reduced diameter to a second, enlarged diameter; and
    a perfusion conduit extending through said inflatable balloon, at least a portion of said perfusion conduit expandable from a first reduced diameter to a second enlarged diameter;
    wherein said second, enlarged diameter of said perfusion conduit is larger than the first, reduced outer diameter of said deflated balloon.

2. A balloon catheter as in claim 1, further comprising a tubular support for maintaining said perfusion conduit in the second enlarged diameter.

3. A balloon catheter as in claim 2, wherein the support is movable from a first position proximal of the balloon to a second position within a portion of the perfusion conduit extending through the balloon.

4. A balloon catheter as in claim 3, further comprising a control for moving said support from the first to the second position.

5. A method of treating a site in a body lumen, comprising the steps of:
    providing a catheter of the type having an elongate, flexible, tubular body, a dilatation balloon on the body, and at least one influent port on a first side of the balloon in fluid communication with at least one effluent port on a second side of the balloon, said influent and effluent ports in fluid communication with each other by way of a central lumen extending through the catheter;
    positioning the catheter within a body lumen so that the balloon is adjacent a treatment site;
    inflating the balloon to treat the site; and
    holding the central lumen open to resist collapse and optimize fluid flow therethrough, wherein said holding step comprises positioning a support structure within the lumen to maintain patency of the lumen by moving the support structure from a proximal insertion position to a distal perfusion position within the central lumen.

6. A catheter comprising:
    an elongate, flexible, tubular body;
    a central lumen extending through at least a portion of the body;
    at least one influent port extending through the wall of the tubular body and communicating with said central lumen;
    at least one effluent port extending through the wall of the tubular body and communicating with the central lumen;
    wherein the central lumen is expandable from a first, reduced fluid flow capacity to a second, increased fluid capacity; and
    a support for maintaining the central lumen in the second, increased fluid flow capacity;
    wherein said support is axially moveable from a first, proximal position to a second, distal position, wherein said distal position is within said central lumen.

7. A catheter as in claim 6, wherein said support comprises a spring coil.

* * * * *